(12) United States Patent
Scarborough et al.

(10) Patent No.: US 7,678,790 B2
(45) Date of Patent: *Mar. 16, 2010

(54) PLATELET ADP RECEPTOR INHIBITORS

(75) Inventors: Robert M. Scarborough, Half Moon Bay, CA (US); Hans-Michael Jantzen, San Francisco, CA (US); Wolin Huang, Foster City, CA (US); David M. Sedlock, Burlingame, CA (US); Charles Marlowe, Redwood City, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 124 days.

This patent is subject to a terminal disclaimer.

(21) Appl. No.: 11/286,259

(22) Filed: Nov. 23, 2005

(65) Prior Publication Data
US 2007/0155719 A1 Jul. 5, 2007

Related U.S. Application Data

(63) Continuation of application No. 10/759,396, filed on Jan. 15, 2004, now Pat. No. 7,022,731, which is a continuation of application No. 10/350,883, filed on Jan. 23, 2003, now Pat. No. 6,689,786, which is a continuation of application No. 09/775,812, filed on Feb. 5, 2001, now abandoned.

(60) Provisional application No. 60/230,447, filed on Sep. 6, 2000, provisional application No. 60/202,072, filed on May 5, 2000, provisional application No. 60/180,208, filed on Feb. 4, 2000.

(51) Int. Cl.
| | |
|---|---|
| *C07D 417/12* | (2006.01) |
| *C07D 411/12* | (2006.01) |
| *C07D 417/14* | (2006.01) |
| *C07D 401/04* | (2006.01) |
| *A61K 31/40* | (2006.01) |
| *A61K 31/38* | (2006.01) |
| *A61K 31/44* | (2006.01) |
| *A61K 31/425* | (2006.01) |
| *A61K 31/495* | (2006.01) |
| *A61K 31/55* | (2006.01) |

(52) U.S. Cl. .............. 514/222.8; 514/231.5; 514/259.4; 514/292; 514/293; 514/309; 514/414; 514/444; 514/445; 544/250; 544/285; 546/81; 546/82; 546/83; 546/141; 546/142; 548/465; 549/65

(58) Field of Classification Search ................ 544/284, 544/285; 514/266.2, 266.24, 266.3, 222.8, 514/231.5, 259.4, 292, 293, 309, 414, 444, 514/445; 549/65; 546/81, 82, 83, 141, 142; 548/465

See application file for complete search history.

(56) References Cited

U.S. PATENT DOCUMENTS

| 3,847,925 A | 11/1974 | Beregi et al. |
| 5,475,025 A | 12/1995 | Tjoeng et al. |

FOREIGN PATENT DOCUMENTS

| WO | WO 94/19341 | 9/1994 |
| WO | WO 94/21602 | 9/1994 |
| WO | WO 99/36425 | 7/1999 |
| WO | WO 01/57037 A | 8/2001 |

OTHER PUBLICATIONS

Holland (Journal of Organic Chemistry (1961), 26, 1662-5).*
Plotnikova et al., "Arenesulfonamides. LXXX. Aroylarenesulfonamides." Retrieved from STN Database accession No. 82:139564 XP002215531 abstract, Database CA Online! Chemical Abstracts Service, Columbus Ohio, USA.

* cited by examiner

*Primary Examiner*—Bruck Kifle
(74) *Attorney, Agent, or Firm*—Townsend and Townsend and Crew LLP

(57) ABSTRACT

Novel compounds of formula (I) to (VI), which more particularly include sulfonylurea derivatives, sulfonylthiourea derivatives, sulfonylguanidine derivatives, sulfonylcyanoguanidine derivatives, thioacylsulfonamide derivatives, and acylsulfonamide derivatives which are effective platelet ADP receptor inhibitors. These derivatives may be used in various pharmaceutical compositions, and are particularly effective for the prevention and/or treatment of cardiovascular diseases, particularly those diseases related to thrombosis. The invention also relates to a method for preventing or treating thrombosis in a mammal comprising the step of administering a therapeutically effective amount of a compound of formulae (I)-(VI), or a pharmaceutically acceptable salt thereof.

9 Claims, No Drawings

PLATELET ADP RECEPTOR INHIBITORS

FIELD OF THE INVENTION

The invention relates to novel compounds of formula (I), formula (II), formula (III), formula (IV), formula (V) and formula (VI) (hereinafter referred to as "formulae (I)-(VI)"), which more particularly include sulfonylurea derivatives, sulfonylthiourea derivatives, sulfonylguanidine derivatives, sulfonylcyanoguanidine derivatives, thioacylsulfonamide derivatives, and acylsulfonamide derivatives which are effective platelet ADP receptor inhibitors. These derivatives may be used in various pharmaceutical compositions, and are particularly effective for the prevention and/or treatment of cardiovascular diseases, particularly those diseases related to thrombosis.

DESCRIPTION OF THE RELATED ART

Thrombotic complications are a major cause of death in the industrialized world. Examples of these complications include acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura. Thrombotic and restenotic complications also occur following invasive procedures, e.g., angioplasty, carotid endarterectomy, post CABG (coronary artery bypass graft) surgery, vascular graft surgery, stent placements and insertion of endovascular devices and protheses. It is generally thought that platelet aggregates play a critical role in these events. Blood platelets, which normally circulate freely in the vasculature, become activated and aggregate to form a thrombus with disturbed blood flow caused by ruptured atherosclerotic lesions or by invasive treatments such as angioplasty, resulting in vascular occlusion. Platelet activation can be initiated by a variety of agents, e.g., exposed subendothelial matrix molecules such as collagen, or by thrombin which is formed in the coagulation cascade.

An important mediator of platelet activation and aggregation is ADP (adenosine 5'-diphosphate) which is released from blood platelets in the vasculature upon activation by various agents, such as collagen and thrombin, and from damaged blood cells, endothelium or tissues. Activation by ADP results in the recruitment of more platelets and stabilization of existing platelet aggregates. Platelet ADP receptors mediating aggregation are activated by ADP and some of its derivatives and antagonized by ATP (adenosine 5'-triphosphate) and some of its derivatives (Mills, D. C. B. (1996) *Thromb. Hemost.* 76:835-856). Therefore, platelet ADP receptors are members of the family of P2 receptors activated by purine and/or pyrimidine nucleotides (King, B. F., Townsend-Nicholson, A. & Burnstock, G. (1998) *Trends Pharmacol. Sci.* 19:506-514).

Recent pharmacological data using selective antagonists suggests that ADP-dependent platelet aggregation requires activation of at least two ADP receptors (Kunapuli, S. P. (1998), *Trends Pharmacol. Sci.* 19:391-394; Kunapuli S. P. & Daniel, J. L. (1998) *Biochem. J.* 336:513-523; Jantzen, H. M. et al. (1999) *Thromb. Hemost.* 81:111-117). One receptor appears to be identical to the cloned $P2Y_1$ receptor, mediates phospholipase C activation and intracellular calcium mobilization and is required for platelet shape change. The second platelet ADP receptor important for aggregation mediates inhibition of adenylyl cyclase. Molecular cloning of the gene or cDNA for this receptor has not yet been reported. Based on its pharmacological and signaling properties this receptor has been provisionally termed $P2Y_{ADP}$ (Fredholm, B. B. et al. (1997) *TIPS* 18:79-82), $P2T_{AC}$ (Kunapuli S. P. (1998), *Trends Pharmacol. Sci.* 19:391-394) or P2Ycyc (Hechler, B. et al. (1998) *Blood* 92, 152-159).

Various directly or indirectly acting synthetic inhibitors of ADP-dependent platelet aggregation with antithrombotic activity have been reported. The orally active antithrombotic thienopyridines ticlopidine and clopidogrel inhibit ADP-induced platelet aggregation, binding of radiolabeled ADP receptor agonist 2-methylthioadenosine 5'-diphosphate to platelets, and other ADP-dependent events indirectly, probably via formation of an unstable and irreversible acting metabolite (Quinn, M. J. & Fitzgerald, D. J. (1999) *Circulation* 100:1667-1667). Some purine derivatives of the endogenous antagonist ATP, e.g., AR-C (formerly FPL or ARL) 67085MX and AR-C69931MX, are selective platelet ADP receptor antagonists which inhibit ADP-dependent platelet aggregation and are effective in animal thrombosis models (Humphries et al. (1995), *Trends Pharmacol. Sc.* 16, 179; Ingall, A. H. et al. (1999) *J. Med. Chem.* 42, 213-230). Novel triazolo[4,5-d]pyrimidine compounds have been disclosed as $P_{2T}$-antagonists (WO 99/05144). Tricyclic compounds as platelet ADP receptor inhibitors have also been disclosed in WO 99/36425. The target of these antithrombotic compounds appears to be the platelet ADP receptor mediating inhibition of adenylyl cyclase.

Despite these compounds, there exists a need for more effective platelet ADP receptor inhibitors. In particular, there is a need for platelet ADP receptor inhibitors having antithrombotic activity that are useful in the prevention and/or treatment of cardiovascular diseases, particularly those related to thrombosis.

SUMMARY OF THE INVENTION

The invention provides compounds of formula (I), formula (II), formula (III), formula (IV), formula (V) and formula (VI):

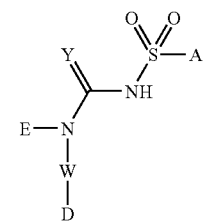

I

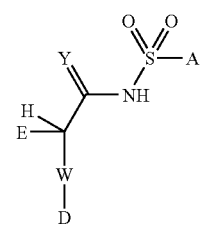

II

-continued

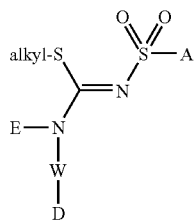
III

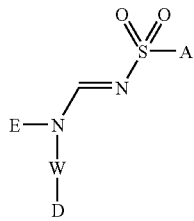
IV

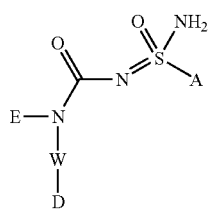
V

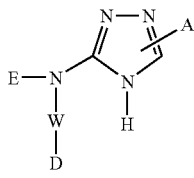
VI

A is selected from the group consisting of aryl, substituted aryl, heteroaryl, substituted heteroaryl, alkylaryl, and alkylheteroaryl.

W is selected from the group consisting of aryl, substituted aryl, heteroaryl, and substituted heteroaryl.

E is selected from the group consisting of H, —$C_1$-$C_8$ alkyl, polyhaloalkyl, —$C_{3-8}$-cycloalkyl, aryl, alkylaryl, substituted aryl, heteroaryl, and substituted heteroaryl.

D is selected from the group consisting of NR$^1$—(C=O)—R$^2$, —O—R$^1$;

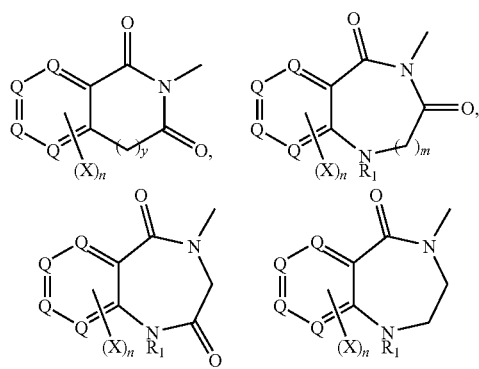

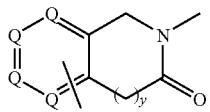 and 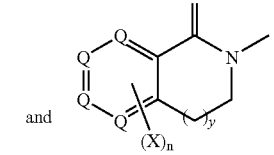

wherein:

R$^1$ is independently selected from the group consisting of:
H, $C_1$-$C_8$ alkyl polyhaloalkyl, —$C_{3-8}$-cycloalkyl, aryl, alkylaryl, substituted aryl, heteroaryl, substituted heteroaryl —(C=O)—$C_1$-$C_8$ alkyl —(C=O)-aryl, —(C=O)-substituted aryl, —(C=O)-heteroaryl and —(C=O)-substituted heteroaryl;

R$^2$ is independently selected from the group consisting of aryl substituted aryl heteroaryl substituted heteroaryl, or R$^1$ and R$^2$ can be direct linked or can be indirectly linked through a carbon chain that is from 1 to about 8 carbon atoms in length, n is 0-4, m is 0 or 1, y is 0-4 and Q is independently C or N, with the proviso that when Q is a ring carbon atom, each ring carbon atom is independently substituted by X.

X is in each case a member independently selected from the group consisting of:
H, halogen, polyhaloalkyl, —OR$^3$, —SR$^3$, —CN, —NO$_2$, —SO$_2$R$^3$, —$C_{1-10}$-alkyl, —$C_{3-8}$-cycloalkyl, aryl, aryl-substituted by 1-4 R$^3$ groups, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$-alkylamino $C_{1-8}$ alkyl, $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy $C_{1-6}$ alkyloxy, hydroxy, hydroxy $C_{1-6}$ alkyl, and a 5 to 10 membered fused or non-fused aromatic or nonaromatic heterocyclic ring system, having 1 to 4 heteroatoms independently selected from N, O, and S, with the proviso that the carbon and nitrogen atoms, when present in the heterocyclic ring system, are unsubstituted, mono- or di-substituted independently with 0-2 R$^4$ groups.

R$^3$ and R$^4$ are each independently selected from the group consisting of:
H, halogen, —CN, —NO$_2$, —$C_{1-10}$ alkyl $C_{3-8}$-cycloalkyl, aryl, amino, amino-$C_{1-8}$-alkyl, $C_{1-3}$-acylamino, $C_{1-3}$-acylamino-$C_{1-8}$-alkyl, $C_{1-6}$ alkylamino, $C_{1-6}$-alkylamino $C_{1-6}$ alkyl $C_{1-6}$ dialkylamino, $C_{1-6}$ dialkylamino $C_{1-8}$ alkyl, $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy-$C_{1-6}$-alkyloxy, hydroxy, hydroxy-$C_{1-6}$-alkyl, -thio and thio-$C_{1-6}$-alkyl.

Y is selected from the group consisting of O, S, N—OR$^5$, and NR$^5$, wherein R$^5$ is selected from the group consisting of:
H $C_{1-10}$ alkyl $C_{3-8}$-cycloalkyl, and CN.

The invention also covers all pharmaceutically acceptable salts and prodrugs of the compounds of formulae (I)-(VI).

In another aspect, the invention provides pharmaceutical compositions for preventing or treating thrombosis in a mammal containing a therapeutically effective amount of a compound of formulae (I)-(VI) or a pharmaceutically acceptable salt thereof and a pharmaceutically acceptable carrier. The invention further provides a method for preventing or treating thrombosis in a mammal by administering a therapeutically effective amount of a compound of formulae (I)-(VI) or a pharmaceutically acceptable salt thereof.

DETAILED DESCRIPTION OF THE INVENTION

Definitions

In accordance with the present invention and as used herein, the following terms are defined with the following meanings, unless explicitly stated otherwise.

The term "alkenyl" refers to a trivalent straight chain or branched chain unsaturated aliphatic radical. The term "alkinyl" (or "alkynyl") refers to a straight or branched chain aliphatic radical that includes at least two carbons joined by a triple bond. If no number of carbons is specified, alkenyl and alkinyl each refer to radicals having from 2-12 carbon atoms.

The term "alkyl" refers to saturated aliphatic groups including straight-chain, branched-chain and cyclic groups having the number of carbon atoms specified, or if no number is specified, having up to about 12 carbon atoms. The term "cycloalkyl" as used herein refers to a mono-, bi-, or tricyclic aliphatic ring having 3 to about 14 carbon atoms and preferably 3 to about 7 carbon atoms.

The term "$C_1$-$C_6$ alkoxy" as used herein refers to an ether moiety whereby the oxygen is connected to a straight or branched chain of carbon atoms of the number indicated.

The term "mono-$C_1$-$C_6$ alkylamino" as used herein refers to an amino moiety whereby the nitrogen is substituted with one H and one $C_1$-$C_6$ alkyl substituent, the latter being defined as above.

The term "di-$C_1$-$C_6$ alkylamino" as used herein refers to an amino moiety whereby the nitrogen is substituted with two $C_1$-$C_6$ alkyl substituents as defined above.

The term "monoarylamino" as used herein refers to an amino moiety whereby the nitrogen is substituted with one H and one aryl substituent, such as a phenyl, the latter being defined as above.

The term "diarylamino" as used herein refers to an amino moiety whereby the nitrogen is substituted with two aryl substituents, such as phenyl, the latter being defined as above.

The term "$C_1$-$C_6$ alkylsulfonyl" as used herein refers to a dioxosulfur moiety with the sulfur atom also connected to one $C_1$-$C_6$ alkyl substituent, the latter being defined as above.

The term "$C_1$-$C_6$ alkoxycarbonyl" as used herein refers to a hydroxycarbonyl moiety whereby the hydrogen is replaced by a $C_1$-$C_6$ alkyl substituent, the latter being defined as above.

As used herein, the terms "carbocyclic ring structure" and "$C_{3-16}$ carbocyclic mono, bicyclic or tricyclic ring structure" or the like are each intended to mean stable ring structures having only carbon atoms as ring atoms wherein the ring structure is a substituted or unsubstituted member selected from the group consisting of: a stable monocyclic ring which is an aromatic ring ("aryl") having six ring atoms ("phenyl"); a stable monocyclic non-aromatic ring having from 3 to about 7 ring atoms in the ring; a stable bicyclic ring structure having a total of from 7 to about 12 ring atoms in the two rings wherein the bicyclic ring structure is selected from the group consisting of ring structures in which both of the rings are aromatic, ring structures in which one of the rings is aromatic and ring structures in which both of the rings are non-aromatic; and a stable tricyclic ring structure having a total of from about 10 to about 16 atoms in the three rings wherein the tricyclic ring structure is selected from the group consisting of: ring structures in which three of the rings are aromatic, ring structures in which two of the rings are aromatic and ring structures in which three of the rings are non-aromatic. In each case, the non-aromatic rings when present in the monocyclic, bicyclic or tricyclic ring structure may independently be saturated, partially saturated or fully saturated. Examples of such carbocyclic ring structures include, but are not limited to, cyclopropyl, cyclobutyl, cyclopentyl, cyclohexyl, adamantyl, cyclooctyl, [3.3.0]bicyclooctane, [4.3.0]bicyclononane, [4.4.0]bicyclodecane (decalin), 2.2.2]bicyclooctane, fluorenyl, phenyl, naphthyl, indanyl, adamantyl, or tetrahydronaphthyl (tetralin). Moreover, the ring structures described herein may be attached to one or more indicated pendant groups via any carbon atom which results in a stable structure. The term "substituted" as used in conjunction with carbocyclic ring structures means that hydrogen atoms attached to the ring carbon atoms of ring structures described herein may be substituted by one or more of the substituents indicated for that structure if such substitution(s) would result in a stable compound.

The term "aryl" which is included with the term "carbocyclic ring structure" refers to an unsubstituted or substituted aromatic ring, substituted with one, two or three substituents selected from lower alkoxy, lower alkyl, lower alkylamino, hydroxy, halogen, cyano, hydroxyl, mercapto, nitro, thioalkoxy, carboxaldehyde, carboxyl, carboalkoxy and carboxamide, including but not limited to carbocyclic aryl, heterocyclic aryl, and biaryl groups and the like, all of which may be optionally substituted. Preferred aryl groups include phenyl, halophenyl, loweralkylphenyl, napthyl, biphenyl, phenanthrenyl and naphthacenyl.

The term "arylalkyl" which is included with the term "carbocyclic aryl" refers to one, two, or three aryl groups having the number of carbon atoms designated, appended to an alkyl group having the number of carbon atoms designated. Suitable arylalkyl groups include, but are not limited to, benzyl picolyl, naphthylmethyl, phenethyl, benzyhydryl, trityl, and the like, all of which may be optionally substituted.

The term "phenyl" as used herein refers to a six carbon containing aromatic ring which can be variously mono- or poly-substituted with H $C_1$-$C_6$ alkyl, hydroxyl, $C_1$-$C_6$ alkoxy, amino, mono-$C_1$-$C_6$ alkylamino, di-$C_1$-$C_6$ alkylamino, nitro, fluoro, chloro, bromo, iodo, hydroxycarbonyl, or $C_1$-$C_6$ alkoxycarbonyl.

As used herein, the term "heterocyclic ring" or "heterocyclic ring system" is intended to mean a substituted or unsubstituted member selected from the group consisting of a stable monocyclic ring having from 5-7 members in the ring itself and having from 1 to 4 hetero ring atoms selected from the group consisting of N, O and S; a stable bicyclic ring structure having a total of from 7 to 12 atoms in the two rings wherein at least one of the two rings has from 1 to 4 hetero atoms selected from N, O and S, including bicyclic ring structures wherein any of the described stable monocyclic heterocyclic rings is fused to a hexane or benzene ring; and a stable tricyclic heterocyclic ring structure having a total of from 10 to 16 atoms in the three rings wherein at least one of the three rings has from 1 to 4 hetero atoms selected from the group consisting of N, O and S. Any nitrogen and sulfur atoms present in a heterocyclic ring of such a heterocyclic ring structure may be oxidized. Unless indicated otherwise the terms "heterocyclic ring" or "heterocyclic ring system" include aromatic rings, as well as non-aromatic rings which can be saturated, partially saturated or fully saturated nonaromatic rings. Also, unless indicated otherwise the term "heterocyclic ring system" includes ring structures wherein all of the rings contain at least one hetero atom as well as structures having less than all of the rings in the ring structure containing at least one hetero atom, for example bicyclic ring structures wherein one ring is a benzene ring and one of the rings has one or more hetero atoms are included within the term "heterocyclic ring systems" as well as bicyclic ring structures wherein each of the two rings has at least one hetero atom. Moreover, the ring structures described herein may be attached to one or more indicated pendant groups via any hetero atom or carbon atom which results in a stable structure. Further, the term "substituted" means that one or more of the hydrogen atoms on the ring carbon atom(s) or nitrogen atom(s) of the each of the rings in the ring structures described herein may be replaced by one or more of the indicated substituents if such replacement(s) would result in a stable compound. Nitrogen atoms in a ring structure may be quaternized, but such compounds are specifically indicated or are included within the term "a pharmaceutically acceptable salt" for a particular compound. When the total number of O and S atoms in a single heterocyclic ring is greater than 1, it is preferred that such atoms not be adjacent to one another. Preferably, there are no more that 1 O or S ring atoms in the same ring of a given heterocyclic ring structure.

Examples of monocyclic and bicyclic heterocyclic ring systems, in alphabetical order, are acridinyl azocinyl benzimidazolyl benzofuranyl benzothiofuranyl benzothiophenyl benzoxazolyl, benzthiazolyl, benztriazolyl benztetrazolyl benzisoxazolyl benzisothiazolyl benzimidazalinyl carbazolyl 4aH-carbazolyl, carbolinyl, chromanyl chromenyl, cinnolinyl decahydroquinolinyl 2H,6H-1,5,2-dithiazinyl, dihydrofuro[2,3-b]tetrahydrofuran, furanyl furazanyl, imidazolidinyl imidazolinyl imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, octahydroisoquinolinyl, oxadiazolyl, 1,2,3-oxadiazolyl, 1,2,4-oxadiazolyl, 1,2,5-oxadiazolyl-1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, 6H-1,2,5-thiadazinyl, 1,2,3-thiadiazolyl, 1,2,4-thiadiazolyl-1,2,5-thiadiazolyl-1,3,4-thiadiazolyl, thianthrenyl, thiazolyl, thienyl, thienothiazolyl, thienooxazolyl, thienoimidazolyl, thiophenyl triazinyl 1,2,3-triazolyl, 1,2,4-triazolyl, 1,2,5-triazolyl 1,3,4-triazolyl and xanthenyl. Preferred heterocyclic ring structures include, but are not limited to, pyridinyl, furanyl, thienyl, pyrrolyl, pyrazolyl, pyrrolidinyl, imidazolyl indolyl, benzimidazolyl, 1H-indazolyl, oxazolinyl, or isatinoyl. Also included are fused ring and spiro compounds containing, for example, the above heterocylic ring structures.

As used herein the term "aromatic heterocyclic ring system" has essentially the same definition as for the monocyclic and bicyclic ring systems except that at least one ring of the ring system is an aromatic heterocyclic ring or the bicyclic ring has an aromatic or non-aromatic heterocyclic ring fused to an aromatic carbocyclic ring structure.

The terms "halo" or "halogen" as used herein refer to Cl, Br, F or I substituents. The term "haloalkyl", and the like, refer to an aliphatic carbon radicals having at least one hydrogen atom replaced by a Cl, Br, F or I atom, including mixtures of different halo atoms. Trihaloalkyl includes trifluoromethyl and the like as preferred radicals, for example.

The term "methylene" refers to —CH$_2$—.

The term "pharmaceutically acceptable salts" includes salts of compounds derived from the combination of a compound and an organic or inorganic acid. These compounds are useful in both free base and salt form. In practice, the use of the salt form amounts to use of the base form; both acid and base addition salts are within the scope of the present invention.

"Pharmaceutically acceptable acid addition salt" refers to salts retaining the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicyclic acid and the like.

"Pharmaceutically acceptable base addition salts" include those derived from inorganic bases such as sodium, potassium, lithium, ammonium, calcium, magnesium, iron, zinc, copper, manganese, aluminum salts and the like. Particularly preferred are the ammonium, potassium, sodium, calcium and magnesium salts. Salts derived from pharmaceutically acceptable organic nontoxic bases include salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-diethylaminoethanol, trimethamine, dicyclohexylamine, lysine, arginine, histidine, caffeine, procaine, hydrabamine, choline, betaine, ethylenediamine, glucosamine, methylglucamine, theobromine, purines, piperizine, piperidine, N-ethylpiperidine, polyamine resins and the like. Particularly preferred organic nontoxic bases are isopropylamine, diethylamine, ethanolamine, trimethamine, dicyclohexylamine, choline, and caffeine.

"Biological property" for the purposes herein means an in vivo effector or antigenic function or activity that is directly or indirectly performed by a compound of this invention that are often shown by in vitro assays. Effector functions include receptor or ligand binding, any enzyme activity or enzyme modulatory activity, any carrier binding activity, any hormonal activity, any activity in promoting or inhibiting adhesion of cells to an extracellular matrix or cell surface molecules, or any structural role. Antigenic functions include possession of an epitope or antigenic site that is capable of reacting with antibodies raised against it.

In the compounds of this invention, carbon atoms bonded to four non-identical substituents are asymmetric. Accordingly, the compounds may exist as diastereoisomers, enantiomers or mixtures thereof. The syntheses described herein may employ racemates, enantiomers or diastereomers as starting materials or intermediates. Diastereomeric products resulting from such syntheses may be separated by chromatographic or crystallization methods, or by other methods known in the art. Likewise, enantiomeric product mixtures may be separated using the same techniques or by other methods known in the art. Each of the asymmetric carbon atoms, when present in the compounds of this invention, may be in one of two configurations (R or S) and both are within the scope of the present invention.

Compound Embodiments of the Invention

Compounds of formula (I), formula (II), formula (III), formula (IV), formula (V) and formula (VI) below represent one embodiment of the invention:

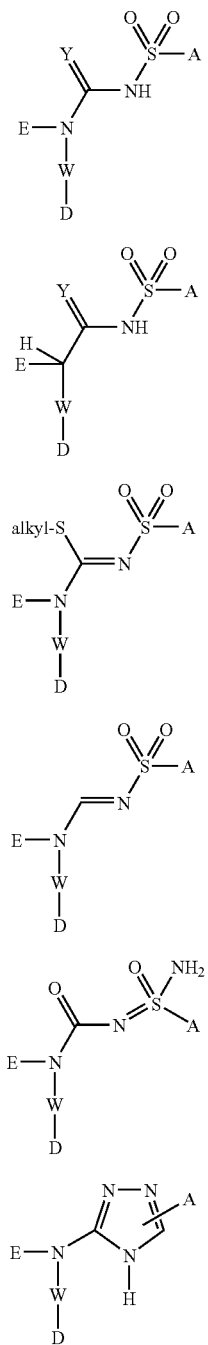

A is selected from the group consisting of aryl, substituted aryl, heteroaryl, substituted heteroaryl, alkylaryl, and alkylheteroaryl.

W is selected from the group consisting of aryl, substituted aryl, heteroaryl, and substituted heteroaryl.

E is selected from the group consisting of H, —$C_1$-$C_8$ alkyl, polyhaloalkyl, —$C_{3-8}$-cycloalkyl, aryl, alkylaryl, substituted aryl, heteroaryl, and substituted heteroaryl.

D is selected from the group consisting of $NR^1$—(C=O)—$R^2$, —O—$R^1$;

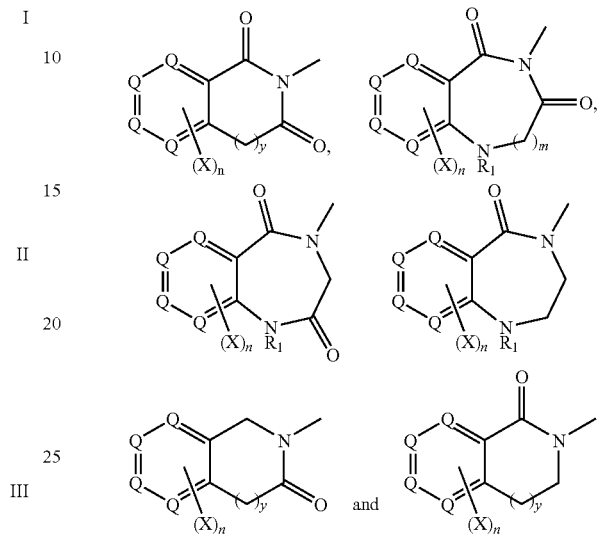

wherein:

$R^1$ is independently selected from the group consisting of:
H, $C_1$-$C_8$ alkyl, polyhaloalkyl, —$C_{3-8}$-cycloalkyl, aryl, alkylaryl, substituted aryl, heteroaryl, substituted heteroaryl, —(C=O)—$C_1$-$C_8$ alkyl, —(C=O)-aryl, —(C=O)-substituted aryl, —(C=O)-heteroaryl and —(C=O)-substituted heteroaryl;

$R^2$ is selected from the group consisting of: aryl, substituted aryl, heteroaryl, substituted heteroaryl, or $R^1$ and $R^2$ can be direct linked or can be indirectly linked through a carbon chain that is from 1 to about 8 carbon atoms in length, n is 0-4, m is 0 or 1, y is 0-4 and Q is independently C or N, with the proviso that when Q is a ring carbon atom, each ring carbon atom is independently substituted by X, wherein X is in each case a member independently selected from the group consisting of H, halogen, polyhaloalkyl, —$OR^3$, —$SR^3$, —CN, —$NO_2$, —$SO_2R^3$, —$C_{1-10}$-alkyl, —$C_{3-8}$-cycloalkyl, aryl, arylsubstituted by 1-4 $R^3$ groups, amino, amino-$C_{1-8}$-alkyl, $C_{1-3}$-acylamino, $C_{1-3}$-acylamino-$C_{1-8}$-alkyl, $C_{1-6}$-alkylamino, $C_{1-6}$-alkylamino $C_{1-8}$ alkyl $C_{1-6}$ dialkylamino, $C_{1-6}$ dialkylamino $C_{1-8}$-alkyl $C_{1-6}$ alkoxy, $C_{1-6}$ alkoxy-$C_{1-6}$-alkyl, carboxy-$C_{1-6}$-alkyl, $C_{1-3}$-alkoxycarbonyl, $C_{1-3}$-alkoxycarbonyl-$C_{1-6}$-alkyl, carboxy $C_{1-6}$ alkyloxy, hydroxy, hydroxy $C_{1-6}$ alkyl, and a 5 to 10 membered fused or non-fused aromatic or nonaromatic heterocyclic ring system, having 1 to 4 heteroatoms independently selected from N, O, and S, with the proviso that the carbon and nitrogen atoms, when present in the heterocyclic ring system, are unsubstituted, mono- or di-substituted independently with 0-2 $R^4$ groups, and wherein $R^3$ and $R^4$ are each independently selected from the group consisting of:

H, halogen, —CN, —NO$_2$, —C$_{1-10}$ alkyl, C$_{3-8}$-cycloalkyl, aryl, amino, amino-C$_{1-8}$-alkyl, C$_{1-3}$-acylamino, C$_{1-3}$-acylamino-C$_{1-8}$-alkyl, C$_{1-6}$-alkylamino, C$_{1-6}$-alkylamino C$_{1-8}$ alkyl, C$_{1-6}$ dialkylamino, C$_{1-6}$ dialkylamino C$_{1-8}$ alkyl C$_{1-6}$ alkoxy, C$_{1-6}$ alkoxy-C$_{1-6}$-alkyl, carboxy-C$_{1-6}$-alkyl, C$_{1-3}$-alkoxycarbonyl, C$_{1-3}$-alkoxycarbonyl-C$_{1-6}$-alkyl, carboxy-C$_{1-6}$-alkyloxy, hydroxy, hydroxy-C$_{1-6}$-alkyl, -thio and thio-C$_{1-6}$-alkyl.

Y is selected from the group consisting of O, S, N—OR$^5$, and NR$^5$, wherein $R^5$ is selected from the group consisting of:

H, C$_{1-10}$ alkyl, C$_{3-8}$-cycloalkyl, and CN.

The invention also covers all pharmaceutically acceptable salts and prodrugs of the compounds of formula I to formula VI.

In another preferred embodiment of the invention, compounds of formulae (I)-(VI) include the compounds set forth below in Tables 1-4:

TABLE 1

Formula Ia

TABLE 1-continued
Formula Ia
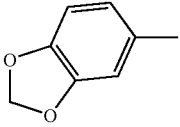
| R₂ | R₁ | W | Y | A |
|---|---|---|---|---|
| 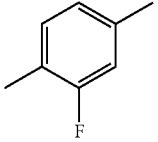 | Me | 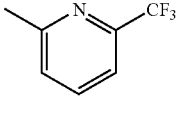 | NH |  |
|  | 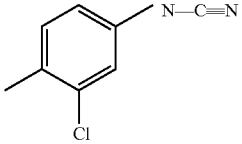 | 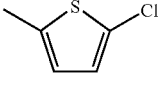 |  | 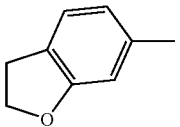 |
| 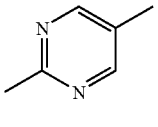 | Me | 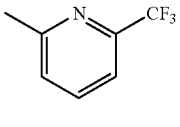 | O | 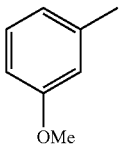 |
| 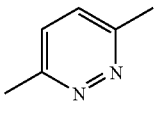 | H | 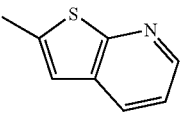 | O | 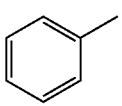 |
| 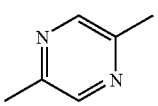 | H | 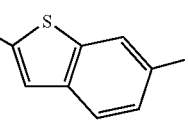 | N-OH | |

TABLE 2
Formula Ib
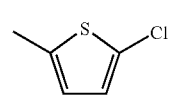
| X | W | Y | A |
|---|---|---|---|
| 3-Br | 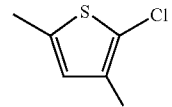 | O | 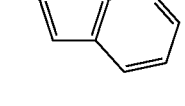 |
| 3-Cl | 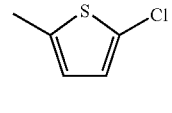 | NH | 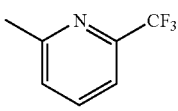 |
| 4-OMe | 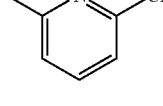 | O | 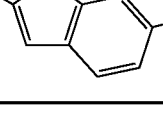 |
| H | 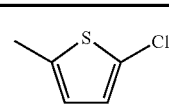 | N—C≡N | 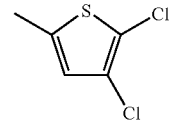 |
| 3,4-diMe | 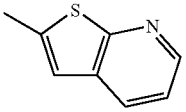 | NH | 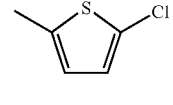 |
| 3-SO₂Me | 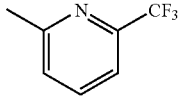 | O |  |
| 3-NMe₂ |  | N—OH |  |
TABLE 3
Formula Ic
| Y | A |
|---|---|
| O |  |
| NH |  |
| O |  |
| N—C≡N |  |
| NH |  |
| O |  |
| N—OH |  |

TABLE 4
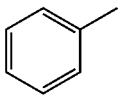
Formula Id
| R₁ | R₂ | W |
|---|---|---|
| H | 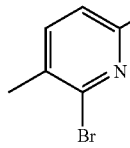 | 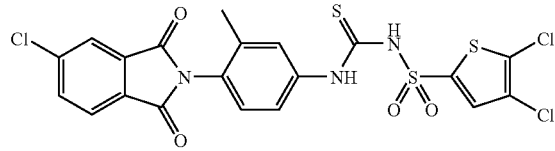 |
| Me | 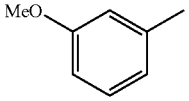 | 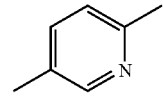 |
| 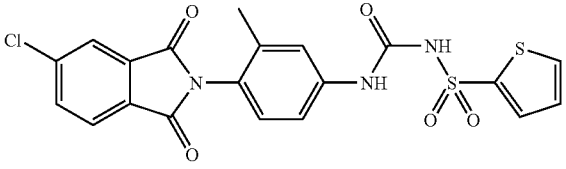 |  | 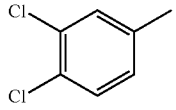 |
| H | 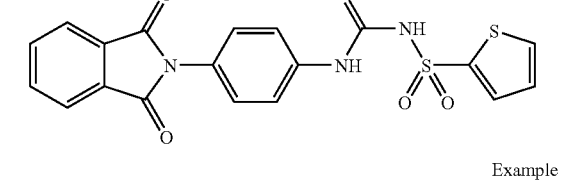 | 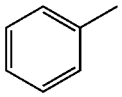 |
| H |  | 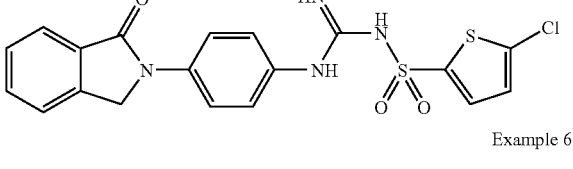 |
| Me | 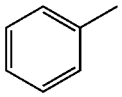 | 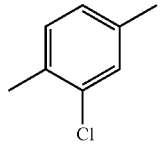 |
| H | 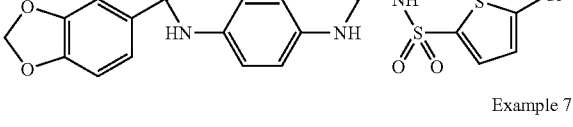 | 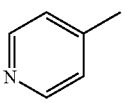 |
Examples of specific preferred compounds are listed below:
Example 1
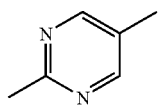
Example 2
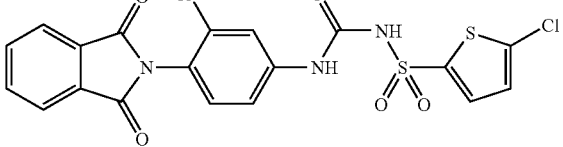
Example 3
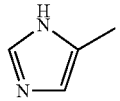
Example 4
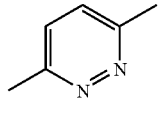
Example 5
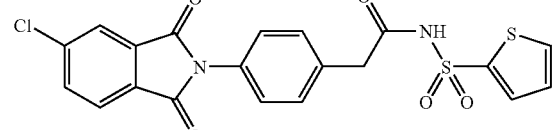
Example 6
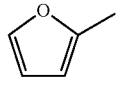
Example 7
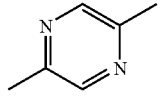
Example 8
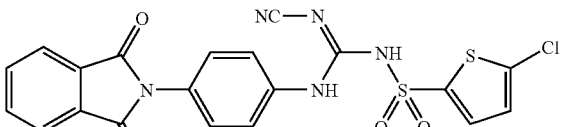
Example 9
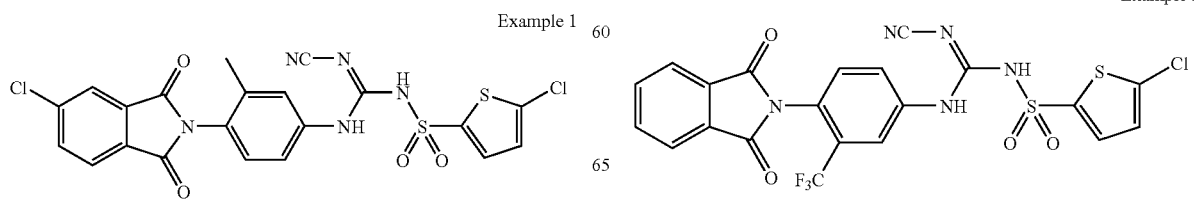

-continued

Example 10
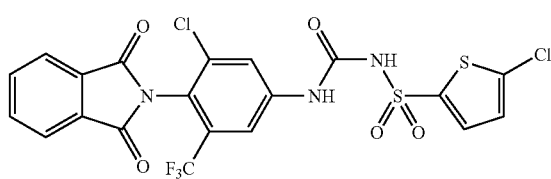

Example 11
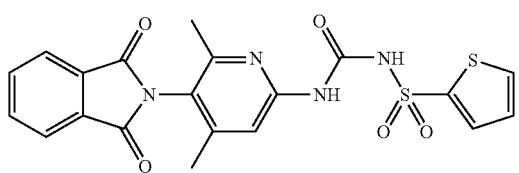

Example 12
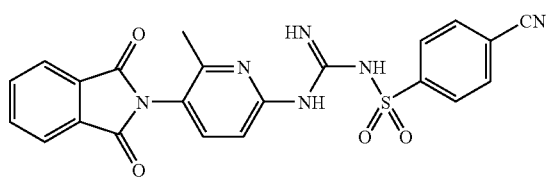

Example 13
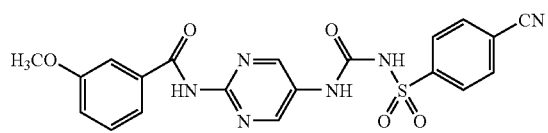

Example 14
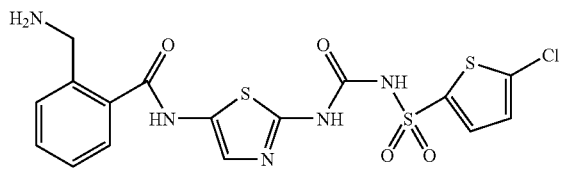

Example 15
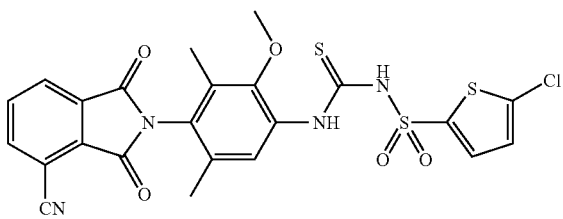

Example 16
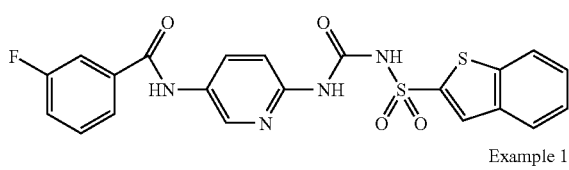

Example 17
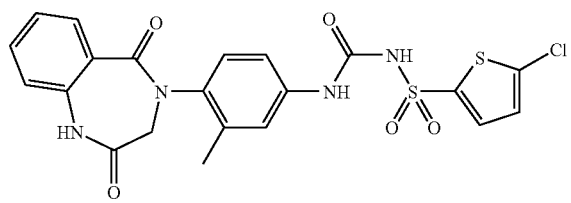

-continued

Example 18
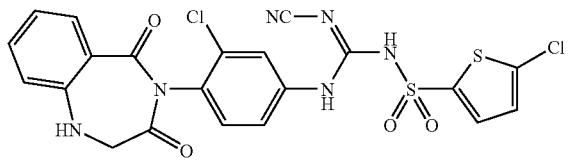

Example 19
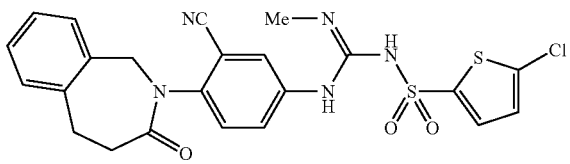

Example 20
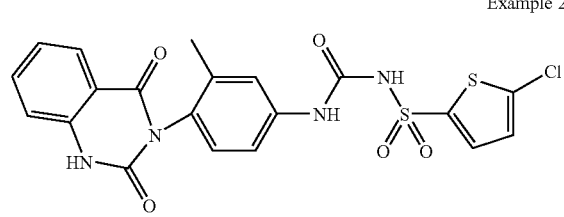

Example 21
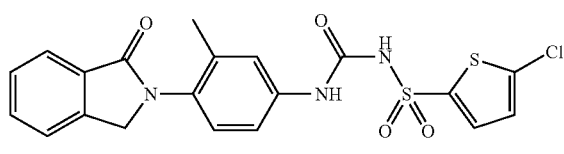

Preparation of Compounds of the Invention

A compound of formulae (I)-(VI) may be prepared by various methods as outlined in the following documents: J. Med. Chem., 33, 23-93-2407 (1990); Biorg. & Med. Chem. Letts., Vol. 2, No. 9, pp. 987-992 (1992); J. Med. Chem., 35, 3012-3016 (1992); U.S. Pat. No. 5,234,955 (1993), U.S. Pat. No. 5,354,778 (1994); U.S. Pat. No. 5,565,494 (1996); U.S. Pat. No. 5,594,028 (1997); U.S. Pat. No. 5,302,724 (1994); and WO 97/08145, which are incorporated herein in their entirety by reference. Other well-known heterocyclic and carbocyclic synthetic procedures as well as modification of the procedures that are incorporated above may be utilized.

Compounds of formulae (I)-(VI) may be isolated using typical isolation and purification techniques known in the art, including, for example, chromatographic and recrystallization methods.

In compounds of formula formulae (I)-(VI) of the invention, carbon atoms to which four non-identical substituents are bonded are asymmetric. Accordingly, a compound of formulae (I)-(VI) may exist as enantiomers, diastereomers or a mixture thereof. The enantiomers and diastereomers may be separated by chromatographic or crystallization methods, or by other methods known in the art. The asymmetric carbon atom when present in a compound of formulae (I)-(VI) of the invention, may be in one of two configurations (R or S) and both are within the scope of the invention. The presence of small amounts of the opposing enantiomer or diastereomer in the final purified product does not affect the therapeutic or diagnostic application of such compounds.

According to the invention, compounds of formulae (I)-(VI) may be further treated to form pharmaceutically acceptable salts. Treatment of a compound of the invention with an acid or base may form, respectively, a pharmaceutically acceptable acid addition salt and a pharmaceutically acceptable base addition salt, each as defined above. Various inorganic and organic acids and bases known in the art including those defined herein may be used to effect the conversion to the salt.

The invention also relates to pharmaceutically acceptable isomers, hydrates, and solvates of compounds of formulae (I)-(VI). Compounds of formulae (I)-(VI) may also exist in various isomeric and tautomeric forms including pharmaceutically acceptable salts, hydrates and solvates of such isomers and tautomers.

This invention also encompasses prodrug derivatives of the compounds of formulae (I)-(VI). The term "prodrug" refers to a pharmacologically inactive derivative of a parent drug molecule that requires biotransformation, either spontaneous or enzymatic, within the organism to release the active drug. Prodrugs are variations or derivatives of the compounds of formulae (I)-(VI) of this invention which have groups cleavable under metabolic conditions. Prodrugs become the compounds of the invention which are pharmaceutically active in vivo when they undergo solvolysis under physiological conditions or undergo enzymatic degradation. Prodrug compounds of this invention may be called single, double, triple, etc., depending on the number of biotransformation steps required to release the active drug within the organism, and indicating the number of functionalities present in a precursor-type form. Prodrug forms often offer advantages of solubility, tissue compatibility, or delayed release in the mammalian organism (Bundgard, *Design of Prodrugs*, pp. 7-9, 21-24, Elsevier, Amsterdam (1985); Silverman, *The Organic Chemistry of drug Design and Drug Action*, pp. 352-401, Academic Press, San Diego, Calif. (1992)). Prodrugs commonly known in the art include acid derivatives well known to practitioners of the art, such as, for example, esters prepared by reaction of the parent acids with a suitable alcohol, or amides prepared by reaction of the parent acid compound with an amine, or basic groups reacted to form an acylated base derivative. Moreover, the prodrug derivatives of this invention may be combined with other features herein taught to enhance bioavailability.

Pharmaceutical Compositions and Methods of Treatment

A compound of formulae (I)-(VI) according to the invention may be formulated into pharmaceutical compositions. Accordingly, the invention also relates to a pharmaceutical composition for preventing or treating thrombosis in a mammal, particularly those pathological conditions involving platelet aggregation, containing a therapeutically effective amount of a compound of formulae (I)-(VI) or a pharmaceutically acceptable salt thereof, each as described above, and a pharmaceutically acceptable carrier or agent. Preferably, a pharmaceutical composition of the invention contains a compound of formulae (I)-(VI), or a salt thereof, in an amount effective to inhibit platelet aggregation, more preferably, ADP-dependent aggregation, in a mammal, in particular, a human. Pharmaceutically acceptable carriers or agents include those known in the art and are described below.

Pharmaceutical compositions of the invention may be prepared by mixing the compound of formulae (I)-(VI) with a physiologically acceptable carrier or agent. Pharmaceutical compositions of the invention may further include excipients, stabilizers, diluents and the like and may be provided in sustained release or timed release formulations. Acceptable carriers, agents, excipients, stabilizers, diluents and the like for therapeutic use are well known in the pharmaceutical field, and are described, for example, in *Remington's Pharmaceutical Sciences*, Mack Publishing Co., ed. A. R. Gennaro (1985). Such materials are nontoxic to the recipients at the dosages and concentrations employed, and include buffers such as phosphate, citrate, acetate and other organic acid salts, antioxidants such as ascorbic acid, low molecular weight (less than about ten residues) peptides such as polyarginine, proteins, such as serum albumin, gelatin, or immunoglobulins, hydrophilic polymers such as polyvinylpyrrolidinone, amino acids such as glycine, glutamic acid, aspartic acid, or arginine, monosaccharides, disaccharides, and other carbohydrates including cellulose or its derivatives, glucose, mannose or dextrins, chelating agents such as EDTA, sugar alcohols such as mannitol or sorbitol, counterions such as sodium and/or nonionic surfactants such as TWEEN, or polyethyleneglycol.

Methods for preventing or treating thrombosis in a mammal embraced by the invention administer a therapeutically effective amount of a compound of formulae (I)-(VI) alone or as part of a pharmaceutical composition of the invention as described above to a mammal, in particular, a human. Compounds of formulae (I)-(VI) and pharmaceutical compositions of the invention containing a compound of formulae (I)-(VI) of the invention are suitable for use alone or as part of a multi-component treatment regimen for the prevention or treatment of cardiovascular diseases, particularly those related to thrombosis. For example, a compound or pharmaceutical composition of the invention may be used as a drug or therapeutic agent for any thrombosis, particularly a platelet-dependent thrombotic indication, including, but not limited to, acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures, e.g., angioplasty, carotid endarterectomy, post CABG (coronary artery bypass graft) surgery, vascular graft surgery, stent placements and insertion of endovascular devices and protheses.

Compounds and pharmaceutical compositions of the invention may also be used as part of a multi-component treatment regimen in combination with other therapeutic or diagnostic agents in the prevention or treatment of thrombosis in a mammal. In certain preferred embodiments, compounds or pharmaceutical compositions of the invention may be coadministered along with other compounds typically prescribed for these conditions according to generally accepted medical practice such as anticoagulant agents, thrombolytic agents, or other antithrombotics, including platelet aggregation inhibitors, tissue plasminogen activators, urokinase, prourokinase, streptokinase, heparin, aspirin, or warfarin. Coadministration may also allow for application of reduced doses of the thrombolytic agents and therefore minimize potential hemorrhagic side-effects. Compounds and pharmaceutical compositions of the invention may also act in a synergistic fashion to prevent reocclusion following a successful thrombolytic therapy and/or reduce the time to reperfusion.

The compounds and pharmaceutical compositions of the invention may be utilized in vivo, ordinarily in mammals such as primates, (e.g., humans), sheep, horses, cattle, pigs, dogs, cats, rats and mice, or in vitro. The biological properties, as defined above, of a compound or a pharmaceutical composition of the invention can be readily characterized by methods that are well known in the art such as, for example, by in vivo studies to evaluate antithrombotic efficacy, and effects on hemostasis and hematological parameters.

Compounds and pharmaceutical compositions of the invention may be in the form of solutions or suspensions. In the management of thrombotic disorders the compounds or pharmaceutical compositions of the invention may also be in such forms as, for example, tablets, capsules or elixirs for oral administration, suppositories, sterile solutions or suspensions or injectable administration, and the like, or incorporated into shaped articles. Subjects (typically mammalian) in need of treatment using the compounds or pharmaceutical compositions of the invention may be administered dosages that will provide optimal efficacy. The dose and method of administration will vary from subject to subject and be dependent upon such factors as the type of mammal being treated, its sex, weight, diet, concurrent medication, overall clinical condition, the particular compound of formulae (I)-(VI) employed, the specific use for which the compound or pharmaceutical composition is employed, and other factors which those skilled in the medical arts will recognize.

Dosage formulations of compounds of formulae (I)-(VI), or pharmaceutical compositions contain a compound of the invention, to be used for therapeutic administration must be sterile. Sterility is readily accomplished by filtration through sterile membranes such as 0.2 micron membranes, or by other conventional methods. Formulations typically will be stored in a solid form, preferably in a lyophilized form. While the preferred route of administration is orally, the dosage formulations of compounds of formulae (I)-(VI) or pharmaceutical compositions of the invention may also be administered by injection, intravenously (bolus and/or infusion), subcutaneously, intramuscularly, colonically, rectally, nasally, transdermally or intraperitoneally. A variety of dosage forms may be employed as well including, but not limited to, suppositories, implanted pellets or small cylinders, aerosols, oral dosage formulations and topical formulations such as ointments, drops and dermal patches. The compounds of formulae (I)-(VI) and pharmaceutical compositions of the invention may also be incorporated into shapes and articles such as implants which may employ inert materials such biodegradable polymers or synthetic silicones as, for example, SILASTIC, silicone rubber or other polymers commercially available. The compounds and pharmaceutical compositions of the invention may also be administered in the form of liposome delivery systems, such as small unilamellar vesicles, large unilamellar vesicles and multilamellar vesicles. Liposomes can be formed from a variety of lipids, such as cholesterol stearylamine or phosphatidylcholines.

Therapeutically effective dosages may be determined by either in vitro or in vivo methods. For each particular compound or pharmaceutical composition of the invention, individual determinations may be made to determine the optimal dosage required. The range of therapeutically effective dosages will be influenced by the route of administration, the therapeutic objectives and the condition of the patient. For injection by hypodermic needle, it may be assumed the dosage is delivered into the bodily fluids. For other routes of administration, the absorption efficiency must be individually determined for each compound by methods well known in pharmacology. Accordingly, it may be necessary for the therapist to titer the dosage and modify the route of administration as required to obtain the optimal therapeutic effect.

The determination of effective dosage levels, that is, the dosage levels necessary to achieve the desired result, i.e., platelet ADP receptor inhibition, will be readily determined by one skilled in the art. Typically, applications of a compound or pharmaceutical composition of the invention are commenced at lower dosage levels, with dosage levels being increased until the desired effect is achieved. The compounds and compositions of the invention may be administered orally in an effective amount within the dosage range of about 0.01 to 1000 mg/kg in a regimen of single or several divided daily doses. If a pharmaceutically acceptable carrier is used in a pharmaceutical composition of the invention, typically, about 5 to 500 mg of a compound of formulae (I)-(VI) is compounded with a pharmaceutically acceptable carrier as called for by accepted pharmaceutical practice including, but not limited to, a physiologically acceptable vehicle, carrier, excipient, binder, preservative, stabilizer, dye, flavor, etc. The amount of active ingredient in these compositions is such that a suitable dosage in the range indicated is obtained.

Typical adjuvants which may be incorporated into tablets, capsules and the like include, but are not limited to, binders such as acacia, corn starch or gelatin, and excipients such as microcrystalline cellulose, disintegrating agents like corn starch or alginic acid, lubricants such as magnesium stearate, sweetening agents such as sucrose or lactose, or flavoring agents. When a dosage form is a capsule, in addition to the above materials it may also contain liquid carriers such as water, saline, or a fatty oil. Other materials of various types may be used as coatings or as modifiers of the physical form of the dosage unit. Sterile compositions for injection can be formulated according to conventional pharmaceutical practice. For example, dissolution or suspension of the active compound in a vehicle such as an oil or a synthetic fatty vehicle like ethyl oleate, or into a liposome may be desired. Buffers, preservatives, antioxidants and the like can be incorporated according to accepted pharmaceutical practice.

Pharmacological Assays

The pharmacological activity of each of the compounds according to the invention is determined by the following in vitro assays:

1. Inhibition of ADP-Mediated Platelet Aggregation In Vitro

The effect of testing the compound according to the invention on ADP-induced human platelet aggregation is preferably assessed in 96-well microtiter assay (see generally the procedures in Jantzen, H. M. et al. (1999) *Thromb. Hemost.* 81:111-117). Human venous blood is collected from healthy, drug-free volunteers into ACD (85 mM sodium citrate, 111 mM glucose, 71.4 mM citric acid) containing $PGI_2$ (1.25 ml ACD containing 1.6 µM $PGI_2$/10 ml blood; $PGI_2$ was from Sigma, St. Louis, Mo.). Platelet-rich plasma (PRP) is prepared by centrifugation at 160×g for 20 minutes at room temperature. Washed platelets are prepared by centrifuging PRP for 10 minutes at 730 g and resuspending the platelet pellet in CGS (13 mM sodium citrate, 30 mM glucose, 120 mM NaCl; 2 ml CGS/10 ml original blood volume) containing 1 U/ml apyrase (grade V, Sigma, St. Louis, Mo.). After incubation at 37° C. for 15 minutes, the platelets are collected by centrifugation at 730 g for 10 minutes and resuspended at a concentration of $3 \times 10^8$ platelets/ml in Hepes-Tyrode's buffer (10 mM Hepes, 138 mM NaCl, 5.5 mM glucose, 2.9 mM KCl, 12 mM $NaHCO_3$, pH 7.4) containing 0.1% bovine serum albumin, 1 mM $CaCl_2$ and 1 mM $MgCl_2$. This platelet suspension is kept >45 minutes at 37° C. before use in aggregation assays.

Inhibition of ADP-dependent aggregation is preferably determined in 96-well flat-bottom microtiter plates using a microtiter plate shaker and plate reader similar to the procedure described by Frantantoni et al., *Am. J. Clin. Pathol.* 94, 613 (1990). All steps are performed at room temperature. The total reaction volume of 0.2 ml/well includes in Hepes-Tyrodes buffer/0.1% BSA: $4.5 \times 10^7$ apyrase-washed platelets, 0.5 mg/ml human fibrinogen (American Diagnostica, Inc., Greenwich, Conn.), serial dilutions of test compounds (buffer for control wells) in 0.6% DMSO. After about 5 minutes preincubation at room temperature, ADP is added to a final concentration of 2 µM which induces submaximal aggregation. Buffer is added instead of ADP to one set of control wells (ADP⁻ control). The OD of the samples is then determined at 490 nm using a microtiter plate reader (Softmax, Molecular Devices, Menlo Park, Calif.) resulting in the 0 minute reading. The plates are then agitated for 5 min on a microtiter plate shaker and the 5 minute reading is obtained in the plate reader. Aggregation is calculated from the decrease of OD at 490 nm at t=5 minutes compared to t=0 minutes and is expressed as % of the decrease in the ADP control samples after correcting for changes in the unaggregated control samples.

II. Inhibition of [³H]2-MeS-ADP Binding to Platelets

Having first determined that the compounds according to the invention inhibit ADP-dependent platelet aggregation with the above assay, a second assay is used to determine whether such inhibition is mediated by interaction with platelet ADP receptors. Utilizing the second assay the potency of inhibition of such compounds with respect to [³H]2-MeS-ADP binding to whole platelets is determined. [³H]2-MeS-ADP binding experiments are routinely performed with outdated human platelets collected by standard procedures at hospital blood banks. Apyrase-washed outdated platelets are prepared as follows (all steps at room temperature, if not indicated otherwise):

Outdated platelet suspensions are diluted with 1 volume of CGS and platelets pelleted by centrifugation at 1900×g for 45 minutes. Platelet pellets are resuspended at 3-6×10⁹ platelets/ml in CGS containing 1 U/ml apyrase (grade V, Sigma, St. Louis, Mo.) and incubated for 15 minutes at 37° C. After centrifugation at 730×g for 20 minutes, pellets are resuspended in Hepes-Tyrode's buffer containing 0.1% BSA (Sigma, St. Louis, Mo.) at a concentration of 6.66×10⁸ platelets/ml. Binding experiments are performed after >45 minutes resting of the platelets.

Alternatively, binding experiments are performed with fresh human platelets prepared as described in I. (Inhibition of ADP-Mediated Platelet Aggregation in vitro), except that platelets are resuspended in Hepes-Tyrode's buffer containing 0.1% BSA (Sigma, St. Louis, Mo.) at a concentration of 6.66×10⁸ platelets/ml. Very similar results are obtained with fresh and outdated platelets.

A platelet ADP receptor binding assay using the tritiated potent agonist ligand [³H]2-MeS-ADP (Jantzen, H. M. et al. (1999) Thromb. Hemost. 81:111-117) has been adapted to the 96-well microtiter format. In an assay volume of 0.2 ml Hepes-Tyrode's buffer with 0.1% BSA and 0.6% DMSO, 1×10⁸ apyrase-washed platelets are preincubated in 96-well flat bottom microtiter plates for 5 minutes with serial dilutions of test compounds before addition of 1 nM [³H]2-MeS-ADP ([³H]2-methylthioadenosine-5'-diphosphate, ammonium salt; specific activity 48-49 Ci/mmole, obtained by custom synthesis from Amersham Life Science, Inc., Arlington Heights, Ill., or NEN Life Science Products, Boston, Mass.). Total binding is determined in the absence of test compounds. Samples for nonspecific binding may contain 10⁻⁵ M unlabelled 2-MeS-ADP (RBI, Natick, Mass.). After incubation for 15 minutes at room temperature, unbound radioligand is separated by rapid filtration and two washes with cold (4-8° C.) Binding Wash Buffer (10 mM Hepes pH 7.4, 138 mM NaCl) using a 96-well cell harvester (Minidisc 96, Skatron Instruments, Sterling, Va.) and 8×12 GF/C glass-fiber filtermats (Printed Filtermat A, for 1450 Microbeta, Wallac Inc., Gaithersburg, Md.). The platelet-bound radioactivity on the filtermats is determined in a scintillation counter (Microbeta 1450, Wallac Inc., Gaithersburg, Md.). Specific binding is determined by subtraction of non-specific binding from total binding, and specific binding in the presence of test compounds is expressed as % of specific binding in the absence of test compounds dilutions.

It should be understood that the foregoing discussion, embodiments and examples merely present a detailed description of certain preferred embodiments. It will be apparent to those of ordinary skill in the art that various modifications and equivalents can be made without departing from the spirit and scope of the invention. All the patents, journal articles and other documents discussed or cited above are herein incorporated by reference.

The invention claimed is:

1. A compound of formula (I):

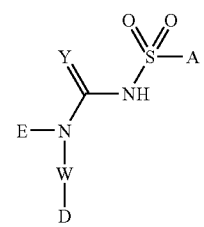

wherein:
A is thienyl; optionally substituted with halogen or cyano;
W is phenylene, optionally substituted with halogen;
E is selected from the group consisting of H, —C₁-C₈alkyl, polyhaloalkyl, —C₃₋₈-cycloalkyl, aryl, alkylaryl and heteroaryl;
D is —NR¹—(C=O)—R²;
R¹ independently selected from the group consisting of: H, —C₁-C₈alkyl, polyhaloalkyl, —C₃-C₈-cycloalkyl, aryl, alkylaryl, heteroaryl, —(C=O)—C₁-C₈ alkyl, —(C=O)-aryl, and —(C=O)-heteroaryl;
R² is independently selected from the group consisting of aryl, and heteroaryl, optionally substituted with lower alkoxy, lower alkylamino or halogen;
each heteroaryl is independently selected from the group consisting of acridinyl, azocinyl benzimidazolyl benzofuranyl benzothiofuranyl benzothiophenyl benzoxazolyl, benzthiazolyl, benztriazolyl benztetrazolyl benzisoxazolyl benzisothiazolyl benzimidazalinyl carbazolyl 4aH-carbazolyl, chromanyl chromenyl, cinnolinyl, furanyl furazanyl, imidazolidinyl imidazolinyl imidazolyl, 1H-indazolyl, indolinyl, indolizinyl, indolyl, 3H-indolyl, isobenzofuranyl, isochromanyl, isoindazolyl, isoindolinyl, isoindolyl, isoquinolinyl (benzimidazolyl), isothiazolyl, isoxazolyl, morpholinyl, naphthyridinyl, oxadiazolyl, 1,2,3-oxadiazolyl, 1,2,4-oxadiazolyl, 1,2,5-oxadiazolyl-1,3,4-oxadiazolyl, oxazolidinyl, oxazolyl, oxazolidinyl, pyrimidinyl, phenanthridinyl, phenanthrolinyl, phenazinyl, phenothiazinyl, phenoxathiinyl, phenoxazinyl, phthalazinyl, pteridinyl, purinyl, pyrazinyl, pyroazolidinyl, pyrazolinyl, pyrazolyl, pyridazinyl, pryidooxazole, pyridoimidazole, pyridothiazole, pyridinyl, pyridyl, pyrimidinyl, pyrrolidinyl, pyrrolinyl 2H-pyrrolyl, pyrrolyl, quinazolinyl, quinolinyl, 4H-quinolizinyl, quinoxalinyl, quinuclidinyl, tetrahydroisoquinolinyl, tetrahydroquinolinyl, 6H-1,2,5-thiadazinyl, 1,2,3-thiadiazolyl, 1,2,4-thiadiazolyl-1,2,5-thiadiazolyl-1,3,4-thiadiazolyl, thianthrenyl, thiazolyl, thienyl, thienothiazolyl, thienooxazolyl, thienoimidazolyl, thiophenyl triazinyl 1,2,3-triazolyl, 1,2,4-triazolyl, 1,2,5-triazolyl 1,3,4-triazolyl and xanthenyl;

$R^1$ and $R^2$ can be direct linked or can be indirectly linked through a carbon chain that is from 1 to about 8 carbon atoms in length;

Y is selected from the group consisting of O, S, N—$OR^5$, and $NR^5$, $R^5$ is selected from the group consisting of: H, $C_{1-10}$ alkyl, $C_{3-8}$-cycloalkyl, and CN;

or pharmaceutically acceptable salts.

2. A compound of claim 1, having the following formula:

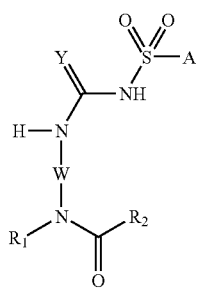

wherein:

$R_2$ is selected from the group consisting of:

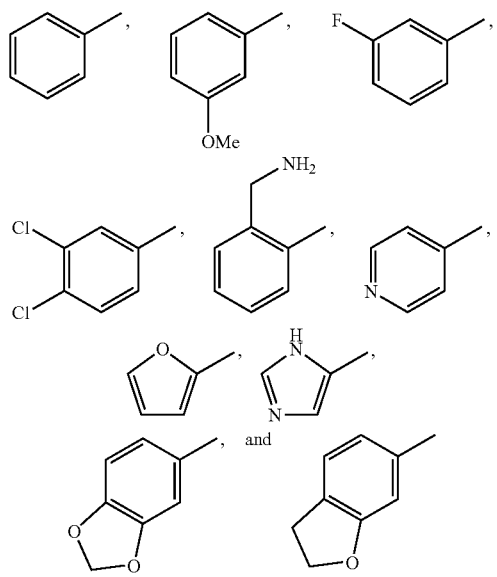

$R_1$ is selected from the group consisting of:
H, Me and

W is selected from the group consisting of:

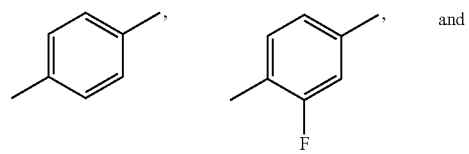

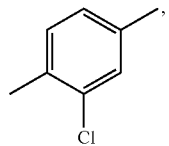

Y is selected from the group consisting of:
O, S, N—C≡N, NH and

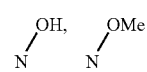

and
A is selected from the group consisting of:

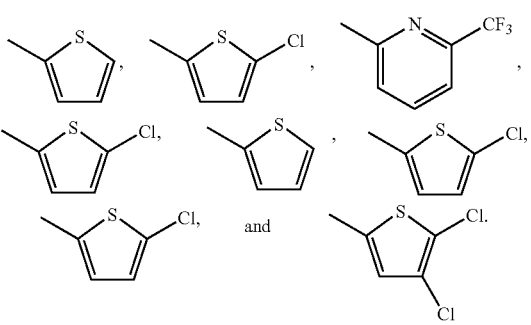

3. A compound of claim 1, having the following formula:

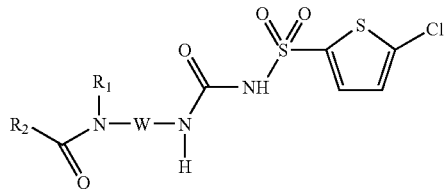

wherein $R_1$ is selected from the group consisting of:
H, Me and

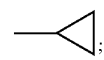

$R_2$ is selected from the group consisting of:

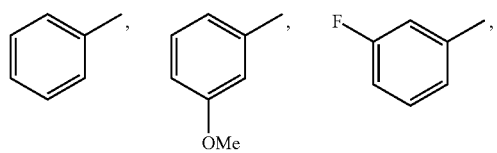

-continued

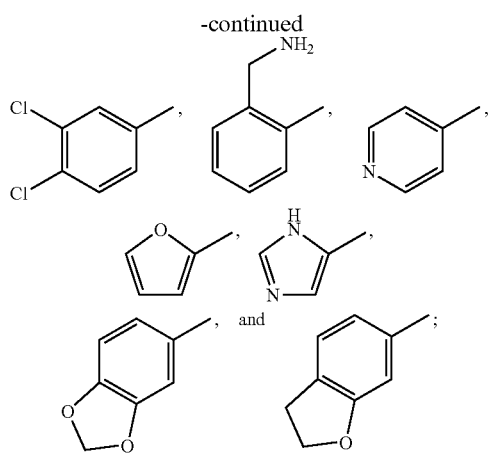

W is selected from the group consisting of:

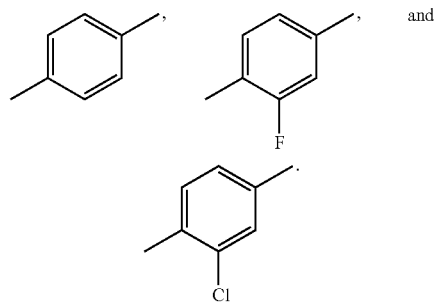

4. A compound of claim 1, selected from the group consisting of:

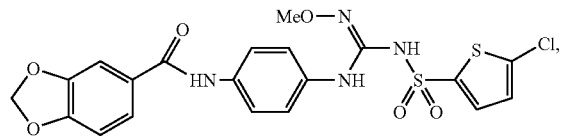

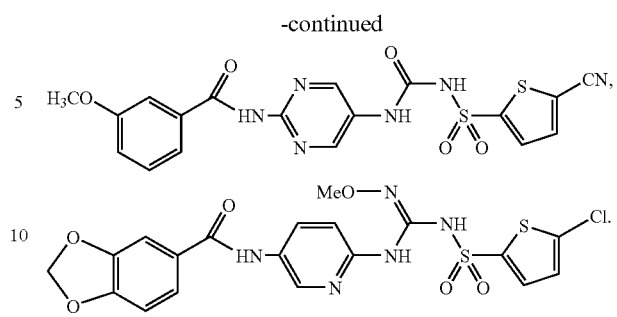

5. A pharmaceutical composition comprising a therapeutically effective amount of a compound according to any one of claims 1 to 4, or a pharmaceutically acceptable salt thereof, and a pharmaceutically acceptable carrier.

6. A pharmaceutical composition of claim 5, wherein said therapeutically effective amount is an amount effective to inhibit platelet aggregation in the mammal.

7. A method for preventing or treating thrombosis in a mammal comprising the step of administering to a mammal a therapeutically effective amount of a compound of claim 1 or a pharmaceutically acceptable salt thereof.

8. A method of claim 7, wherein said mammal is a human.

9. A method of claim 7, wherein said cardiovascular disease is at least one selected from the group consisting of acute myocardial infarction, unstable angina, chronic stable angina, transient ischemic attacks, strokes, peripheral vascular disease, preeclampsia/eclampsia, deep venous thrombosis, embolism, disseminated intravascular coagulation and thrombotic cytopenic purpura, thrombotic and restenotic complications following invasive procedures resulting from angioplasty, carotid endarterectomy, post CABG (coronary artery bypass graft) surgery, vascular graft surgery, stent placements and insertion of endovascular devices and protheses.

* * * * *